(12) United States Patent  
Cherkinsky et al.

(10) Patent No.: US 8,545,223 B1  
(45) Date of Patent: Oct. 1, 2013

(54) DENTAL IMPLANT SYSTEM

(76) Inventors: Jordan Michael Cherkinsky, Coral Springs, FL (US); Stanley Myron Kilman, Boca Raton, FL (US)

( * ) Notice: Subject to any disclaimer, the term of this patent is extended or adjusted under 35 U.S.C. 154(b) by 0 days.

(21) Appl. No.: 13/572,580

(22) Filed: Aug. 10, 2012

Related U.S. Application Data

(60) Provisional application No. 61/665,889, filed on Jun. 28, 2012.

(51) Int. Cl.
*A61C 8/00* (2006.01)

(52) U.S. Cl.
USPC .......................................................... 433/174

(58) Field of Classification Search
USPC ...................................... 433/172–174, 201.1
See application file for complete search history.

(56) References Cited

U.S. PATENT DOCUMENTS

| | | | | |
|---|---|---|---|---|
| 4,011,602 A | * | 3/1977 | Rybicki et al. | 623/23.76 |
| 4,588,381 A | * | 5/1986 | Caracciolo | 433/173 |
| 4,622,010 A | * | 11/1986 | Koch | 433/173 |
| 5,004,421 A | * | 4/1991 | Lazarof | 433/173 |
| 5,470,230 A | * | 11/1995 | Daftary et al. | 433/174 |
| 5,489,210 A | * | 2/1996 | Hanosh | 433/173 |
| 5,611,688 A | * | 3/1997 | Hanosh | 433/174 |
| 5,681,167 A | * | 10/1997 | Lazarof | 433/174 |
| 5,725,378 A | * | 3/1998 | Wang | 433/173 |
| 5,766,009 A | * | 6/1998 | Jeffcoat | 433/173 |
| 5,890,902 A | * | 4/1999 | Sapian | 433/173 |
| 5,931,674 A | * | 8/1999 | Hanosh et al. | 433/173 |
| 6,142,782 A | * | 11/2000 | Lazarof | 433/174 |
| 6,227,856 B1 | * | 5/2001 | Beaty et al. | 433/172 |
| 6,332,778 B1 | * | 12/2001 | Choung | 433/173 |
| 6,340,300 B1 | * | 1/2002 | Padros Fradera | 433/174 |
| 6,506,051 B2 | * | 1/2003 | Levisman | 433/173 |
| 6,939,135 B2 | * | 9/2005 | Sapian | 433/174 |
| 7,300,282 B2 | * | 11/2007 | Sapian | 433/173 |
| 2005/0042574 A1 | * | 2/2005 | Lazarof | 433/174 |
| 2010/0055646 A1 | * | 3/2010 | Zhao | 433/174 |

* cited by examiner

*Primary Examiner* — Cris L Rodriguez
*Assistant Examiner* — Mirayda A Aponte

(57) ABSTRACT

A dental implant system is hermetically sealed and uses a radially extruded extension retentive design. The implant system provides additional retention and resistance to rotational and lateral forces and disperses these forces vertically and apically through the implant body. The implant system also provides protection from issues of sepsis at the junction between the abutment and the implant body, when can result in significant bone loss in conventional designs. The implant system integrates/unifies the components to result in a closer approximation to a natural tooth root to improve resistance to lateral and rotational forces that challenge the integrity of conventional implants. The implant system provides a shorter average length in proportion to its retentive surface area, thereby effectively reducing the needed length to avoid invading nearby anatomic structures, such as the maxillary sinus, mental foramen and/or mandibular canal.

10 Claims, 4 Drawing Sheets

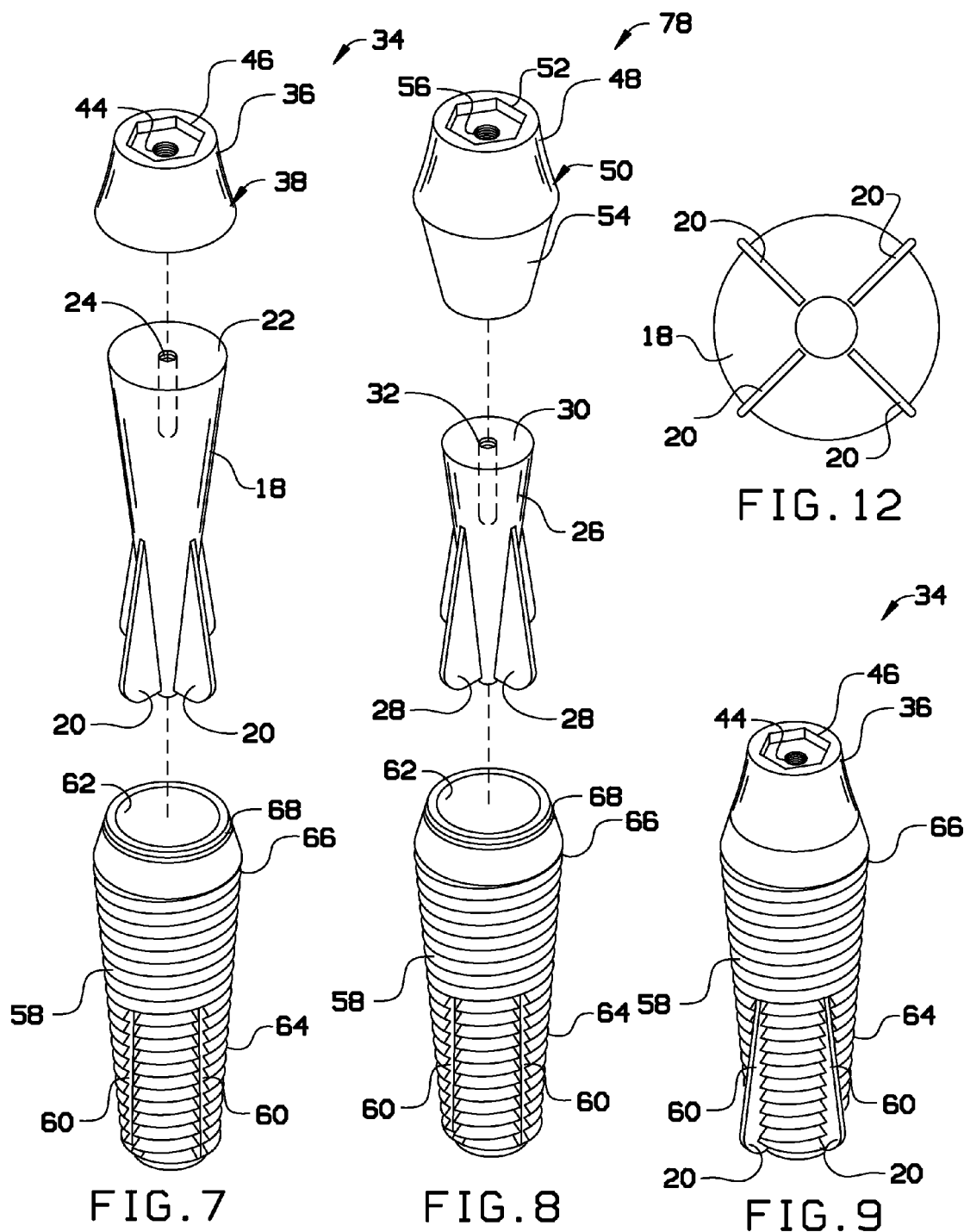

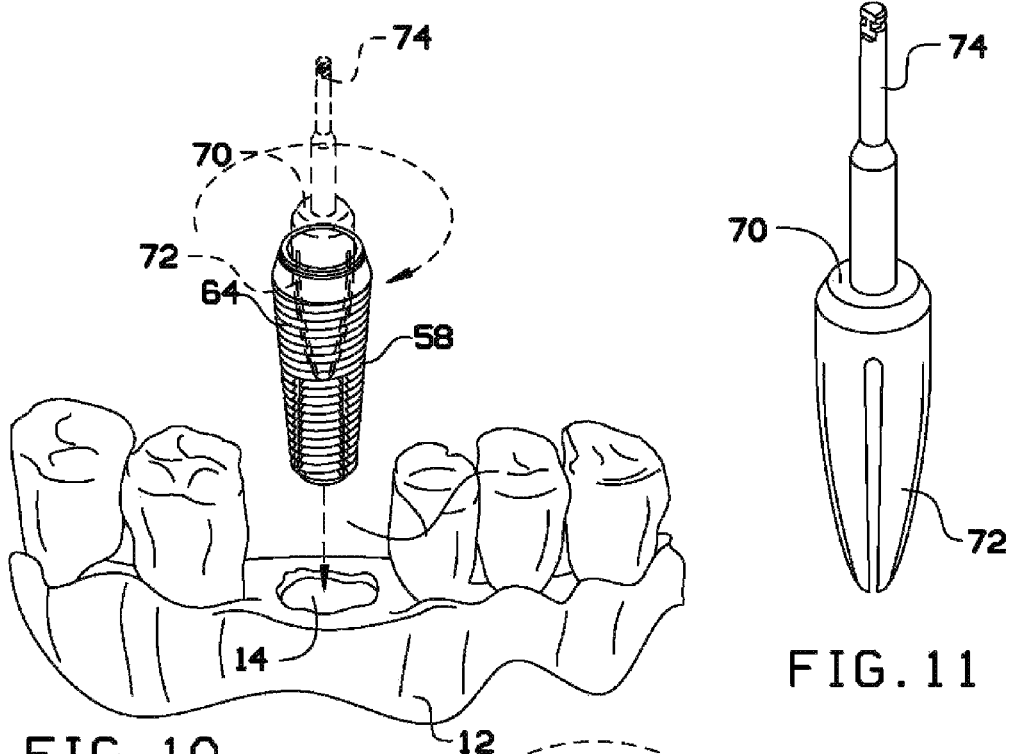
FIG. 10
FIG. 11
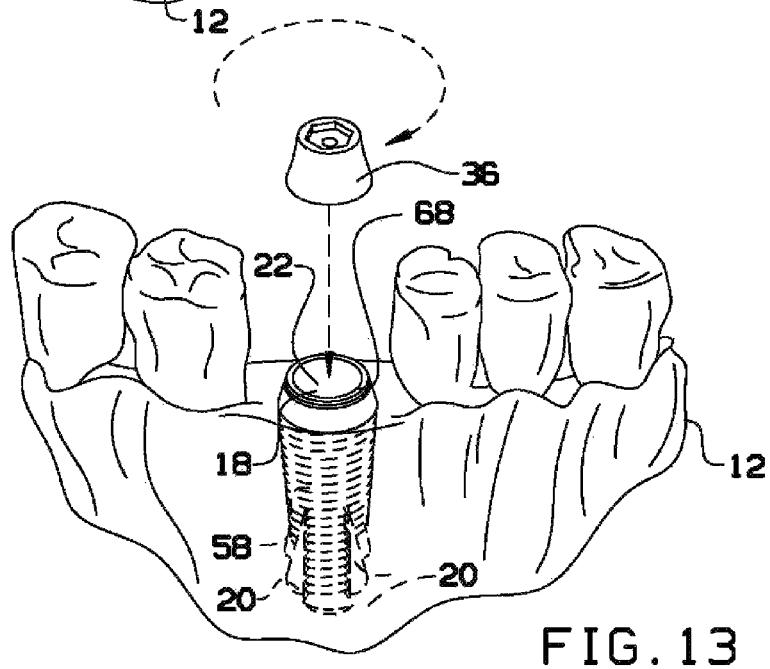
FIG. 13

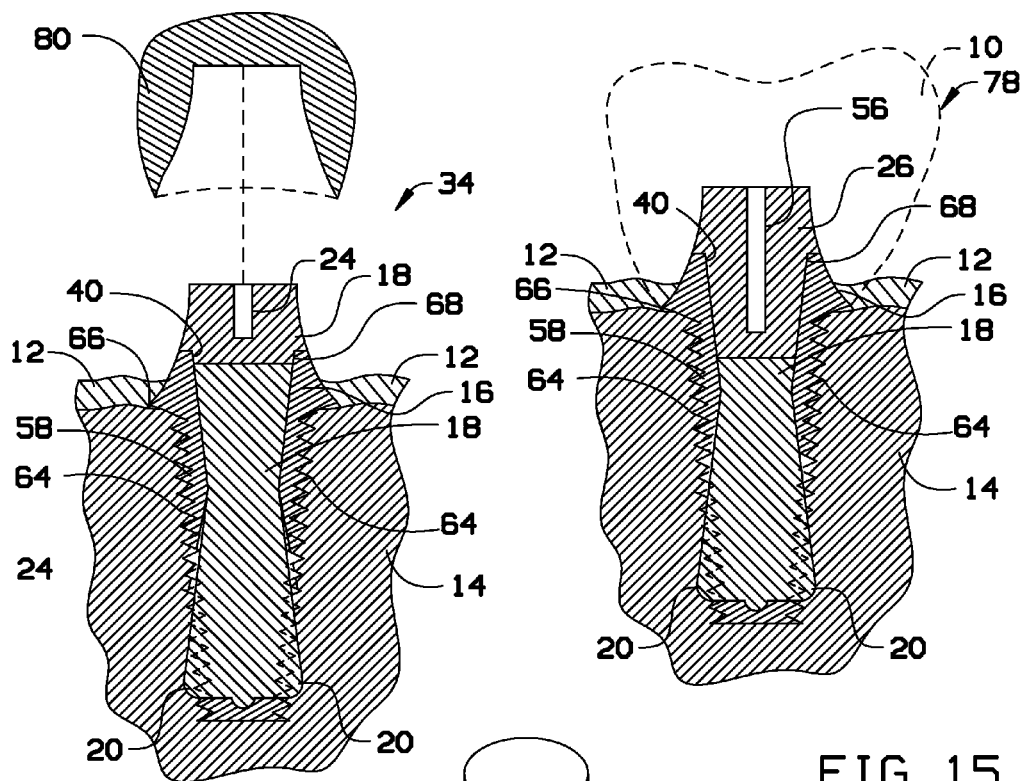
FIG.14
FIG.15
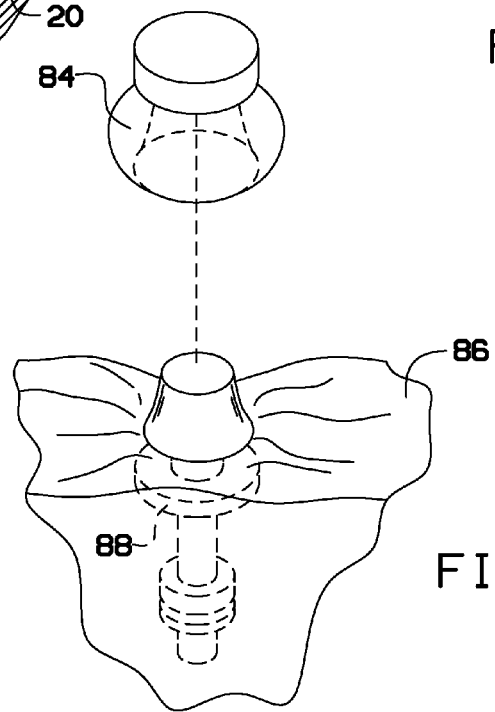
FIG.16

DENTAL IMPLANT SYSTEM

CROSS-REFERENCE TO RELATED APPLICATIONS

This application claims the benefit of priority of U.S. provisional patent application No. 61/665,889, filed Jun. 28, 2012, the contents of which are herein incorporated by reference.

BACKGROUND OF THE INVENTION

The present invention relates to dental implant systems and, more particularly, to a three-component dental implant system that is hermetically sealed and uses an extruded extension retention design.

Conventional implants have less predictable solutions to resist rotation and lateral forces. The distribution of forces is relied upon to be borne by a diminutive screw in concert with an internal butt joint design that does not reliably direct the forces apically. With conventional implants, there are no provisions to extend a crown or a custom abutment onto the implant body, therefore the lateral or rotational forces can result in avulsion of the implant abutment. This may be the result of a broken or loosened screw, and quite possibly a fractured implant body. Conventional implants also do not have predictable solutions to prevent sepsis at the interface of the abutment and the implant body.

As can be seen, there is a need for an improved dental implant system that addresses many of these issues seen with conventional dental implants.

SUMMARY OF THE INVENTION

In one aspect of the present invention, an implant system comprises an implant body having an hollow abutment cavity formed therein; implant body threads formed about an exterior portion of the implant body; implant body extension slots formed longitudinally in a lower portion of the implant body; implant body male threads formed on a top end of the implant body; an insert adapted to fit into the hollow abutment cavity, the insert having insert extensions configured to protrude through the implant body extension slots; and an abutment having female threads to mate with the implant body male threads.

In another aspect of the present invention, an implant system comprises an implant body having an hollow abutment cavity formed therein; implant body threads formed about an exterior portion of the implant body; implant body extension slots formed longitudinally in a lower portion of the implant body; implant body male threads formed on a top end of the implant body; an insert adapted to fit into the hollow abutment cavity, the insert having insert extensions configured to protrude through the implant body extension slots; an abutment having female threads to mate with the implant body male threads; a chamfer body line formed below the implant body male threads, where the abutment seals against the chamfer body line when the abutment female threads are engaged with the implant body male threads; an abutment hexagonal recess for wrench access formed in a top portion of the abutment; an abutment threaded convenience channel formed through the abutment; and an insert threaded convenience channel formed into the insert from a coronal face thereof, the insert threaded convenience channel aligning with the abutment threaded convenience channel.

These and other features, aspects and advantages of the present invention will become better understood with reference to the following drawings, description and claims.

BRIEF DESCRIPTION OF THE DRAWINGS

FIG. 7 is an exploded perspective view of a unified dental implant system standard assembly according to an exemplary embodiment of the present invention;

FIG. 8 is an exploded perspective view of a unified dental implant system modified assembly according to an exemplary embodiment of the present invention;

FIG. 9 is a perspective view of an assembled unified dental implant system, either the standard assembly or modified assembly, of FIGS. 7 and 8;

FIG. 10 is an exploded perspective view showing insertion of the implant body of FIG. 2 into an exemplary gingival/bone tapping utilizing the implant body driver tool (FIG. 11);

FIG. 11 is a perspective view of an implant body driver tool;

FIG. 12 is an apical depiction showing the standard and/or modified assembly insert extensions protruding from the implant body;

FIG. 13 is an exploded perspective view showing the insertion of the standard abutment of FIG. 5 into the implant body of FIG. 3;

FIG. 14 is a cross-sectional view showing application of a resin surgical gingival contouring coping over the standard assembly of FIG. 7;

FIG. 15 is a cross-sectional view showing the modified assembly of FIG. 8 with an outline of a crown;

FIG. 16 is a perspective view of a custom abutment CAD key used with a custom abutment transfer analog according to an exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a dental implant system that is hermetically sealed and uses an extruded extension retention design. The implant system provides additional retention and resistance to rotational and lateral forces and disperses these forces vertically and apically through the implant body. The implant system also provides protection from issues of sepsis at the junction between the abutment and the implant body, which can result in significant bone loss in conventional designs. The implant system integrates/unifies the components to result in a closer approximation to a natural tooth root to improve resistance to lateral and rotational forces that challenge the integrity of conventional implants. The implant system provides a shorter average length in proportion to its retentive surface area, thereby effectively reducing the needed length to avoid invading anatomic structures, such as the maxillary sinus, mental foramen and/or mandibular canal.

Figure 1:
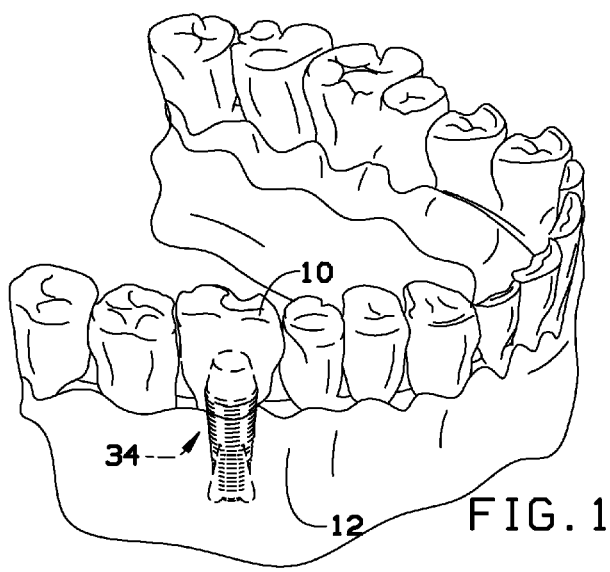
FIG. 1 is a perspective view of a dental implant system in place in a representation of a patient's jaw, according to an exemplary embodiment of the present invention.

Referring now to the Figures, an implant system is shown and described. As shown in FIG. 1, an implant system standard assembly 34 can be formed in a mouth 12 of a patient to secure an implant crown 10.

Figure 2:
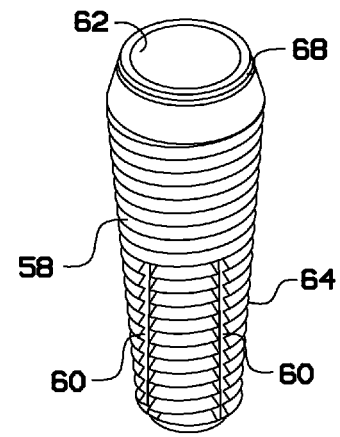
FIG. 2 is a perspective view of an implant body of the implant system of FIG. 1.
Figure 3:
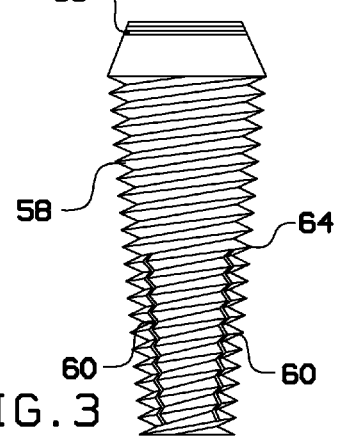
FIG. 3 is a side view of the implant body of FIG. 2.

As shown in FIGS. 2 and 3, the implant system of the present invention (also referred to as the Unified Implant System), an implant body 58 has a rounded and tapered hollow implant abutment cavity 62 formed therein which can be tapered or barrel-shaped. Threads 64 can be formed on the outer surface of the implant body 58. A plurality of extension slots 60, four extension slots 60, can be formed through the implant body 58. The extension slots 60 extend from near a bottom end of the implant body 58 toward a top end of the implant body 58, generally running from about 30 to about 70 percent, typically about 50 percent of the length of the threads 58. Abutment male threads 68 are formed on the coronal or top end of the implant body 58. The male threads 68 are operable to accept an abutment extension, as described in greater detail below, that has a corresponding opposite thread, typically coated with a layer of 24K gold to correct for the tolerances or inaccuracies inherent in all machined device parts and to effectively seal the margin against infectious or noxious agents.

Figure 4:
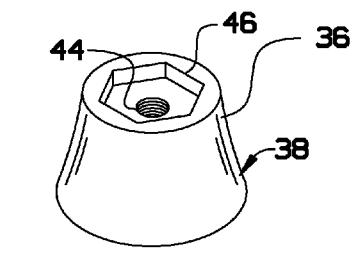
FIG. 4 is a top perspective view of a standard abutment usable with the implant body of FIG. 3.
Figure 5:
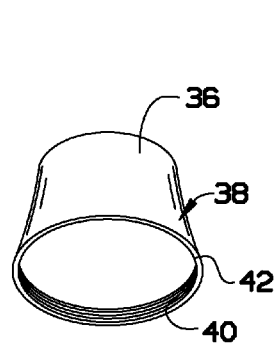
FIG. 5 is a bottom perspective view of the standard abutment of FIG. 4.

Referring now to FIGS. 4 and 5, a standard abutment 36 can include a standard abutment taper surface 38, a standard abutment hexagonal recess 46 for tool access, and a threaded convenience channel 44. Female threads 40 may be disposed on about a cylindrical recess 42 on the bottom side of the abutment 36. The female threads 40 may mate with the male threads 68 on the coronal of the implant body 58. The abutment 36 can thread onto and abut against implant body 58, reducing the probability that sepsis will invade the assembled implant.

Figure 6:
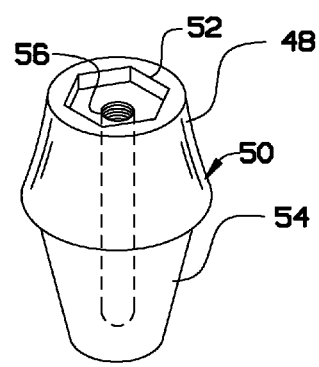
FIG. 6 is a perspective view of a modified abutment usable with the implant body of FIG. 3.
Figure 17:
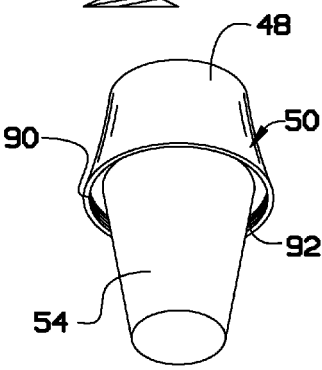
FIG. 17 is a bottom perspective view of the modified abutment of FIG. 6.

Referring now to FIGS. 6 and 17, a modified abutment 48 can include an abutment taper surface 50, an abutment hexagonal recess 52 for tool access, and a threaded convenience channel 56, similar to the standard abutment 36 described above. A modified abutment lower extension 54 may conically extend from the bottom of the modified abutment 48. The abutment lower extension 54 is adapted to fit into the implant body abutment cavity 62 of the implant body 58. Female threads 92 may be disposed on about a cylindrical recess 90 on the bottom side of the abutment 48. The female threads 92 may mate with the male threads 68 on the coronal of the implant body 58. The abutment 48 can thread onto and abut against implant body 58, reducing the probability that sepsis will invade the assembled implant. The modified abutment is intended to accept a custom fabricated (CAD/CAM) abutment produced in a laboratory, attached through a central threaded channel; referred to as the "convenience channel".

Referring now to FIGS. 7, 8, 9 and 12, a standard insert 18 (FIG. 7) can be placed inside the implant body abutment cavity 62. Insert extensions 20 can be disposed on the standard insert 18 to extend through the implant body extension slots 60 formed in the implant body 58. The standard insert 18 can include a standard insert coronal face 22 and a threaded convenience channel 24 that can align with the abutment threaded convenience channel 44, with no communication between the convenience channels.

Similarly, an insert system modified assembly 78 can include a modified insert 26 (FIG. 8) that can be placed inside the implant body abutment cavity 62. Insert extensions 28 can be disposed on the modified insert 26 to extend through the implant body extension slots 60 formed in the implant body 58. The modified insert 26 can include a modified insert coronal face 30 and a threaded convenience channel 32 that can align with the abutment threaded convenience channel 56, with no communication between these convenience channels.

The female threads 40 of the standard abutment 36 (FIG. 7) or the female threads 92 of the modified abutment 48 (FIG. 8) can be threaded onto the male threads 68 of the implant body 58. As described above, one or both of the female and/or male threads can include a coating, such as a 24K gold coating, which corrects for the tolerances of the threads and effectively seals the margin against infectious or noxious agents.

The result of the assembly 34 of the components—the implant body 58, the insert 18, 26 with insert extensions 20, 28 and the abutment 36, 48—is to redirect both rotational and lateral forces apically or downward, resulting in a ferrule effect. The act of assembly, by threading the abutment, "activates" this effect. The implant system enhanced retention allows for placement of an implant of lesser length, reducing the possibility of invading anatomic structures. The implant body design provides a termination line, or chamfer line, at the coronal portion of this component. This, in effect, provides a veritable "double" ferrule effect, since the crown will seat upon the implant body itself. This will enhance the stability and will likely mimic the natural zone that exists in the sub-gingival region of a pristine natural tooth.

The implant system of the present invention approximates the anatomical function of a natural tooth through its design and integrates or joins all mechanical components, which more closely mimics a natural tooth root more accurately than contemporary conventional implant designs. The implant system of the present invention allows for a path that will provide the restorative dentist to fabricate a more biologically compatible restoration than existing conventional designs.

Referring now to FIGS. 10, 11 and 13-15, to place the implant assembly of the present invention, bone 14 is drilled, tapped and then the implant body 58 is screwed into place, using the implant body driver tool 70, typically including a driver tool extension arm 72 and a driver tool latch 74. The insert 22, 30 can be placed into the implant body 58, with the extensions 20, 28 protruding through the extension slots 60 and into bone adjacent to the implant body 58. The abutment 36, 48 can be threaded upon the implant body 58 using an industry standard driver tool attached to torque wrench.

The surgeon can place, using a permanent dental cement, surgical gingival contouring coping 80 to achieve anatomic gingival healing after placement of implant body, and suturing gingiva into place. This coping 80 sits upon the chamfer body line 66 of a chamfer body region 16 of the implant body 58. After healing for a prescribed period of time, the coping 80 can be removed and impression coping can be placed over the assembled unit by a restorative dentist and an impression is made by conventional impression techniques. A crown 10 can be fabricated by a laboratory in a conventional manner, where a non-custom abutment is acceptable, using the castable (lost wax investment technique) pickup impression coping. The surgical gingival contouring coping 80 can be used to make a temporary crown, being compatible with any resin, temporary or permanent.

Referring to FIGS. 15 and 16, using a custom abutment technique, if the angulation of the implant body 58 is out of perpendicular in relation to adjacent teeth or another implant, a combination of a modified insert and a modified abutment is used for laboratory custom fabricated abutments. With this technique, bone is drilled, tapped and the implant body 58 is screwed in place. A modified insert 26 is installed into the implant body 58, followed by the modified abutment 48. The surgeon can place the coping 80 for anatomic gingival healing. After healing for a prescribed period of time, the coping 80 is removed. A custom abutment CAD key 84 and a custom abutment CAD analog 86 can be used to transfer the relationship of the assembled implant system to a CAD/CAM laboratory for fabrication of a custom designed abutment, using a plaster model or direct computer scan. The custom designed abutment can be sealed against the modified abutment 48 using a 24K O-ring 88 to seal the custom abutment to the abutment and screwed in place, using a specially designed long screw to fix the abutment to the underlying assembly, screw installs into the central screw channel or "convenience channel", 56 as in FIGS. 8 and 15, assembled implant system.

The threaded convenience channel 44, 56, 24, and 32 can be used to accommodate placement and/or retrieval of various components, if needed, using the insert retrieval tool (not depicted). Final restoration with the system is completed with placement of fixed individual or multiple prostheses, such as crowns, fixed partial dentures, fixed full arch prostheses, or removable precision partial, or full precision dentures.

The implant system of the present invention is an integrated, closed system that, once assembled, improves upon conventional implant designs in several ways. The implant system of the present invention resists rotation and lateral forces through integration which induces a ferrule effect by the assembly of the components. The extension of the crown and/or the custom abutment onto the implant body itself reinforces the unity of the system. The final result upon completion with a crown or crown/custom abutment is an implant restoration more analogous to a natural tooth because it is effectively a closed system. Because it is a closed system, a zone at the juncture of the standard crown/abutment and/or custom abutment of relative asepsis is created by the final placement of the implant/restoration system. This zone is more akin to a natural gingival crevice.

Once the abutment (either the standard or modified) is installed, the surgeon has the option to embed it and not have it protrude from the gum, but it is not necessary to do this with the implant system of the present invention. The surgeon can suture in a way as to re-affix, a gingival flap after periodontal or oral surgery, if desired, while conventional implants prescribe embedding the implant, which requires opening it up and flapping the gum, revealing the bone again.

The entire construct, implant body, insert, and insert extensions, that is in direct contact with bone, will osseo-integrate, which is defined as the formation of a direct interface between an implant and bone, without intervening soft tissue. A dental osseo-integrated implant is a type of dental implant defined as an endosteal implant containing interstices into which osteoblasts and supporting connective tissue can migrate. Applied to oral implantology, this refers to bone grown adjacent to the surface without an interposed soft tissue layer. No scar tissue or periodontal ligament fibers are present between the bone and implant surface. Direct contact of bone and implant surface can be verified microscopically, and is a typical and usual of all existing implant designs, including the implant system of the present invention.

While the above refers to dental implant systems, the design of the present invention may be used in other applications. For example, the basic implant design of the present invention can be used in long bone implant technology in lieu of existing affixing devices, such as screws. The implant design of the present invention can be used in various other applications, such as in hip implant devices, in adjunct, fixation devices associated with knee replacement and in shoulder replacement applications.

It should be understood, of course, that the foregoing relates to exemplary embodiments of the invention and that modifications may be made without departing from the spirit and scope of the invention as set forth in the following claims.

What is claimed is:

1. An implant system comprising:
   an implant body having a hollow abutment cavity formed therein;
   implant body threads formed about an exterior portion of the implant body;
   implant body extension slots formed longitudinally in a lower portion of the implant body;
   implant body male threads formed on a top end of the implant body;
   an insert adapted to fit into the hollow abutment cavity, the insert having insert extensions configured to protrude through the implant body extension slots and extend beyond the implant body threads; and
   an abutment having female threads to mate with the implant body male threads,
   wherein the implant body has a rounded and tapered hollow implant abutment cavity, wherein the insert and extensions fits into a top end of the implant body.

2. The implant system of claim 1, further comprising a chamfer body line formed below the implant body male threads, where the abutment seals against the chamfer body line when the abutment female threads are engaged with the implant body male threads.

3. The implant system of claim 1, further comprising an abutment hexagonal recess for wrench access formed in a top portion of the abutment.

4. The implant system of claim 1, further comprising an abutment threaded convenience channel formed through the abutment.

5. The implant system of claim 4, further comprising an insert threaded convenience channel formed into the insert from a coronal face thereof, the insert threaded convenience channel aligning with the abutment threaded convenience channel.

6. The implant system of claim 1, wherein the implant body includes four extension slots and the insert includes four insert extensions fitting into and protruding through the extension slots.

7. The implant system of claim 1, wherein the abutment is a standard abutment having an abutment lower extension extending from a bottom side of the abutment.

8. An implant system comprising:
   an implant body having an hollow abutment cavity formed therein;
   implant body threads formed about an exterior portion of the implant body;
   implant body extension slots formed longitudinally in a lower portion of the implant body;
   implant body male threads formed on a top end of the implant body;
   an insert adapted to fit into the hollow abutment cavity, the insert having insert extensions configured to protrude through the implant body extension slots and extend beyond the implant body threads;
   an abutment having female threads to mate with the implant body male threads;
   a chamfer body line formed below the implant body male threads, where the abutment seals against the chamfer body line when the abutment female threads are engaged with the implant body male threads;

an abutment hexagonal recess for wrench access, as well as additional rotation resistance for both crown and custom abutment, formed in a coronal portion of the abutment;

an abutment threaded convenience channel formed partially through the abutment; and an insert threaded convenience channel formed into the insert from a coronal face thereof, the insert threaded convenience channel aligning with the abutment threaded convenience channel, but not communicating through either the abutment or the insert, wherein the implant body has a rounded and tapered hollow implant abutment cavity, wherein the insert and extensions fits into a top end of the implant body.

9. The implant system of claim 8, wherein the implant body includes four extension slots and the insert includes four insert extensions fitting into and through the extension slots, protruding and engaging adjacent bone structure.

10. The implant system of claim 8, wherein the abutment is a modified abutment having an abutment lower extension extending from a bottom side of the abutment, wherein the convenience channel in a central portion of the modified abutment accepting a screw to affix a custom (CAD/CAM) fabricated abutment.

* * * * *